(12) United States Patent
Reydel et al.

(10) Patent No.: US 10,758,117 B2
(45) Date of Patent: Sep. 1, 2020

(54) ENDOSCOPIC ASSISTANCE DEVICES AND METHODS OF USE

(71) Applicant: Endocages, LLC, West Caldwell, NJ (US)

(72) Inventors: Boris Reydel, West Caldwell, NJ (US); Sergey Kantsevoy, Owings Mills, MD (US)

(73) Assignee: Endocages, LLC, West Caldwell, NJ (US)

( * ) Notice: Subject to any disclaimer, the term of this patent is extended or adjusted under 35 U.S.C. 154(b) by 0 days.

(21) Appl. No.: 15/897,320

(22) Filed: Feb. 15, 2018

(65) Prior Publication Data
US 2018/0228362 A1 Aug. 16, 2018

Related U.S. Application Data

(60) Provisional application No. 62/600,168, filed on Feb. 15, 2017.

(51) Int. Cl.
*A61B 1/32* (2006.01)
*A61B 1/00* (2006.01)
(Continued)

(52) U.S. Cl.
CPC .............. *A61B 1/32* (2013.01); *A61B 1/0055* (2013.01); *A61B 1/00082* (2013.01);
(Continued)

(58) Field of Classification Search
CPC ... A61B 1/32; A61B 1/00082; A61B 1/00091; A61B 1/0055
(Continued)

(56) References Cited

U.S. PATENT DOCUMENTS 1,556,355 A * 10/1925 Roney .................... A61B 1/303
600/104
4,198,960 A * 4/1980 Utsugi ................. A61B 1/0125
600/104
(Continued)

FOREIGN PATENT DOCUMENTS

JP 2006192086 A 7/2006

OTHER PUBLICATIONS

International Search Report and Written Opinion issued in International Application No. PCT/US2018/18275, dated May 8, 2018.
(Continued)

*Primary Examiner* — Jessica Weiss
(74) *Attorney, Agent, or Firm* — Meunier Carlin & Curfman LLC

(57) ABSTRACT

Insufflation is currently considered to be a necessary part of an endoscopic procedure. However, it introduces risks and costs that would be beneficial to eliminate. The endoscopic assistance devices and methods disclosed herein facilitate the performance of endoscopic procedures without insufflation. The devices attach directly or indirectly to the distal end portion of the endoscope. One or more resilient, curved bars extend from the attachment point around an internal void space to form a resilient, curved cage that spreads tissue gently during the advance of the endoscope. The resilient, curved bars define the windows of the cage that enable the visualization of the internal anatomy via a lens on the distal face of the endoscope and the passage of treatment devices from the operative channel of the endoscope.

20 Claims, 6 Drawing Sheets

(51) Int. Cl.
    *A61B 1/005* (2006.01)
    *A61B 1/31* (2006.01)
    *A61B 1/273* (2006.01)
(52) U.S. Cl.
    CPC ...... *A61B 1/00085* (2013.01); *A61B 1/00091* (2013.01); *A61B 1/00101* (2013.01); *A61B 1/00128* (2013.01); *A61B 1/273* (2013.01); *A61B 1/31* (2013.01)
(58) Field of Classification Search
    USPC .................................. 600/201–249, 101–183
    See application file for complete search history.

(56) References Cited

U.S. PATENT DOCUMENTS

| | | | | |
|---|---|---|---|---|
| 4,250,873 | A * | 2/1981 | Bonnet | A61B 1/307 600/104 |
| 4,825,259 | A * | 4/1989 | Berry, Jr. | A61B 1/0008 356/241.4 |
| 5,047,848 | A * | 9/1991 | Krauter | A61B 1/0008 33/501 |
| 5,358,496 | A * | 10/1994 | Ortiz | A61B 17/0218 604/104 |
| 5,716,321 | A * | 2/1998 | Kerin | A61B 1/0008 600/104 |
| 5,873,815 | A * | 2/1999 | Kerin | A61B 1/0008 600/114 |
| 7,485,092 | B1 * | 2/2009 | Stewart | A61B 17/00008 600/104 |
| 9,943,665 | B2 * | 4/2018 | Valeti | A61M 25/0074 |
| 2005/0125004 | A1 | 6/2005 | Bates et al. | |
| 2005/0267332 | A1 * | 12/2005 | Paul | A61B 8/1492 600/127 |
| 2009/0054884 | A1 * | 2/2009 | Farley | A61B 18/1492 606/15 |
| 2010/0023005 | A1 * | 1/2010 | Yamamoto | A61B 18/1445 606/41 |
| 2010/0094327 | A1 | 4/2010 | Milsom et al. | |
| 2011/0251454 | A1 | 10/2011 | Robb et al. | |
| 2013/0231534 | A1 | 9/2013 | Piskun et al. | |
| 2014/0142393 | A1 * | 5/2014 | Piskun | A61M 39/22 600/206 |
| 2014/0288377 | A1 * | 9/2014 | Worrel | A61B 17/3417 600/208 |

OTHER PUBLICATIONS

Weill Cornell Medical College and NewYork-Presbyterian Hospital License Technology to Lumendi, Ltd., Sep. 11, 2015, 3 pages.
Olympus America, Distal Attachments, Jan. 4, 2018, 2 pages.

* cited by examiner

ENDOSCOPIC ASSISTANCE DEVICES AND METHODS OF USE

CROSS REFERENCE TO RELATED APPLICATIONS

This application claims the benefit of U.S. Provisional Application No. 62/600,168, filed Feb. 15, 2017, which is hereby incorporated by reference in its entirety.

TECHNICAL FIELD

The present apparatus embodied relates, in general, to medical devices and in particular, to endoscopy.

BACKGROUND

Endoscopes are well-known in the art and are flexible devices that are inserted into a natural body orifice such as the mouth or anus to provide visual and surgical access to portions of the upper and lower gastrointestinal (GI) tract. Endoscope accessible portions of the lower GI tract, for example, extend from the anus to the small intestine, and during this journey, the flexible endoscope must traverse a torturous, collapsed path through the anus, the rectum, and through the large intestine to the ileocecal opening of the small intestine. The torturous path includes an "S" shaped passage through the rectosigmoid junction and the sigmoid colon, and around several larger than right angled bends of the splenic flexure and hepatic flexure. Additionally, in small bowel enteroscopy, an endoscope must traverse a large torturous convoluted path having multiple "S" shaped passages.

Before insertion of the endoscope, the patient is given drugs to purge matter from the GI tract. Once emptied, the tubular walls of the large intestine can flatten or collapse together into a flattened tubular configuration. The collapsed intestines may inhibit passage of the flat face of the distal end of the endoscope, and the collapsed tissue can inhibit visualization by pressing against or near to a camera mounted within the flat face. To enhance the passage of the endoscope through the collapsed lumen and to improve visualization, insufflation gas is routinely pumped into the patient's GI tract to expand and distend the collapsed tubular tissues. This is the case for both upper and lower GI tract endoscopic procedures. The expanded walls improve visualization and reduce tissue contact with the flat face of the endoscope as it is pushed farther and farther into the insufflated GI tract. The distal portion of the endoscope is steerable, and the insufflated tissue can provide room for the surgeon to visually steer the endoscope through the path ahead.

While insufflation enables the practitioner to better visualize the internal anatomy, it introduces a number of risks to the patient while also increasing the time and cost associated with the endoscopic procedure. The administration of insufflation gas is painful and can cause lengthening of the anatomy and spontaneous perforation. Patients are anesthetized during the procedure and require recovery time, while in the care of the medical facility, to awaken from the anesthesia and purge the insufflation gas. $CO_2$ is commonly used for insufflation as it is more readily absorbed through the patient's intestinal wall to reduce the post-operative recovery time. $CO_2$ gas control systems, $CO_2$ tanks, and $CO_2$ gas heaters must be purchased and maintained in order to provide $CO_2$ as an insufflation gas, adding to the expense of the procedure.

SUMMARY

Insufflation is currently considered to be a necessary part of an upper and lower GI tract endoscopy procedures. However, it introduces risks and costs that would be beneficial to eliminate. The endoscopic assistance devices and methods disclosed herein facilitate the performance of endoscopic procedures without insufflation. The devices attach directly or indirectly to the distal end portion of the endoscope. One or more resilient, curved bars extend from the attachment point around an internal void space to form a resilient, curved cage. The resilient, curved bars define the windows of the cage. The windows enable both the visualization of the internal anatomy via a lens on the distal face of the endoscope and also the passage of treatment devices from the operative channel of the endoscope. The resilience of the bars causes them to push back on the tissue, allowing the cage to function as a tissue retractor to spread tissue aside and further facilitate the advance of the endoscope. The tissue retracting feature also enables movement of the tissue to positions that allow for easier access by a treatment device. Because the endoscopic assistance device does not occupy the operative channel, treatment devices can pass without having to compete with space.

In some embodiments, one or more selected resilient, curved bars extend fully around the internal void of the cage, uninterrupted, to form an arch. First and second ends of the selected bar are attached directly to the endoscope or indirectly to the endoscope via a connecting device. In some embodiments, the greatest width $W_{max}$ of the cage, measured perpendicularly to a longitudinal axis extending through the cage when the cage is in a relaxed position, is not more than about three times the diameter of the endoscope. The bars of the cage are formed of a resilient material, and, in some embodiments, the bars have rounded external surfaces in a transverse cross section.

In some embodiments, the first and second ends of each bar are attached to a connecting device that is positioned around the outer surface of a distal end of the endoscope. In some embodiments, the connecting device can have a length of at most 10 millimeters. In this way, the connecting device does not alter the flexibility of a central or proximal region of the insertion tube of the endoscope.

In some embodiments, the cage includes two or more resilient, curved bars that partially define at least three windows of the cage. The two or more bars of the cage might not cross each other at all, or they may cross each other while remaining independently movable. As an example, a first, inner bar can extend through a loop on a second, outer bar, such that the bars cross each other while remaining independently movable. In some embodiments, the two or more bars of the cage are attached to each other at one or more fixation points. In some embodiments, the cage comprises two or more twisted bars that rotate around each other, wherein first and second ends of each twisted bar are configured to be attached to an endoscope or to a connecting device. A third bar can extend between the two or more twisted bars that rotate around each other.

The endoscopic assistance device can include a retraction mechanism that adjusts the length of the cage, or of one or more bars of the cage. As an example, the retraction mechanism can be an elongated pull wire. The distal end of the pull wire can be fastened to the end portion of the at least one bar and the proximal end of the pull wire can be manipulated by a user to affect the movement of the bar in relation to the distal face of the endoscope.

In some embodiments, at least one bar of the endoscopic assistance device is electrically conductive. The electrically conductive bar or bars can include an insulating coating and at least one gap in the insulating coating for delivering current to an adjacent tissue. The electrically conductive bar can be in electrical communication with a power source. In some embodiments, an electrical wire can extend at least a portion of the length of the endoscope to connect the power source to the at least one electrically conductive bar. In some embodiments, at least one bar is detachable from the cage for use as a staple or an endoclip.

Methods of moving an endoscope through a collapsed lumen using an endoscopic assistance device are also disclosed herein. The methods include providing an endoscope having a resilient, curved cage affixed to the distal end, inserting the endoscope with the resilient, curved cage into the collapsed lumen, moving aside the walls of the collapsed lumen adjacent the distal face of the endoscope using the resilient, curved cage, thereby opening the lumen, visualizing the walls of the lumen via windows at least partially defined by the cage, and advancing the endoscope. The method can be performed without an insufflation step. Some embodiments of the method include rotating the endoscope to adjust the position of one or more resilient, curved bars of the cage. Some embodiments include advancing a treatment device through a window of the resilient, curved cage. The walls of the lumen can be placed under tension or compression using one or more resilient, curved bars of the cage to immobilize and facilitate access to the walls for subsequent treatment. In some embodiments, treatment includes cutting, tweezing, cauterizing, or coagulating the walls of the lumen using the treatment device.

The length of the cage can be adjusted while the endoscope is inserted into the lumen. For example, adjusting the length of the cage includes moving one or more resilient, curved bars of the resilient, curved cage in relation to the distal face of the endoscope.

Some embodiments of the method include treating the walls of the lumen using the cage. Treating the walls of the lumen using the cage can include delivering an electrical current to the walls of the lumen via one or more resilient, curved bars of the cage.

In some embodiments, treating the walls of the lumen can include releasing a resilient, curved bar of the cage into the walls of the lumen and stapling the walls of the lumen using the bar. Stapling the walls of the lumen further can include manipulating the walls of the lumen to ensure proper positioning of the bar.

Some embodiments of the method include inserting a first bar of the cage into the walls of the lumen as an endoclip. Inserting a first bar as an endoclip can include suctioning the walls of the lumen into an interior void of the cage, then releasing the first bar into the walls of the lumen. In some embodiments, a second bar of the cage is retracted into the endoscope to cause the first bar to be released as an endoclip. In these embodiments, the bar can be formed of, for example, a shape memory metal alloy.

Methods of locating gastrointestinal polyps in the collapsed lumen of a gastrointestinal tract are also disclosed herein. The methods include providing an endoscope having a resilient, curved cage affixed to the distal end, inserting the endoscope with the resilient, curved cage into the collapsed lumen, flattening a fold of the collapsed lumen located distal to the distal face of the endoscope using the resilient, curved cage, and scanning the flattened fold for one or more gastrointestinal polyps. In some embodiments, flattening the fold is accomplished by pulling proximally on the wall of the collapsed lumen using the resilient, curved cage. The method can further include removing the one or more located gastrointestinal polyps.

DETAILED DESCRIPTION

Figure 1:
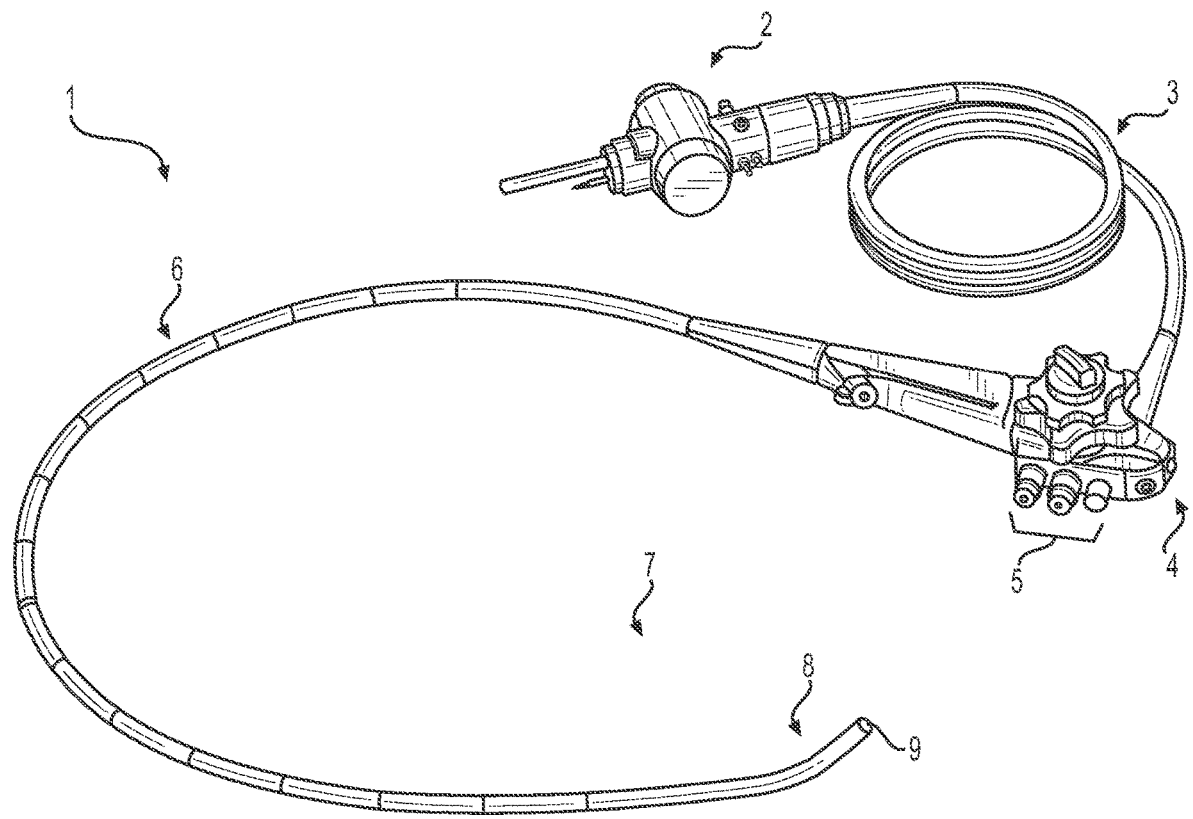
FIG. 1 shows a conventional endoscope.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of the endoscope or the endoscopic assistance device. "Proximal" means a region closest to the light guide connector of the endoscope (and to the practitioner during a procedure), while "distal" means a region farther from the light guide connector of the endoscope (and from the practitioner during a procedure).

The endoscopic assistance devices and methods disclosed herein facilitate the performance of endoscopic procedures without insufflation. Conventional distal endoscope attachments are designed for use in the insufflated bowel. As such, these conventional attachments are larger in diameter than the devices disclosed herein. These conventional distal endoscope attachments are typically cylindrically shaped with a slightly tapered distal edge. This shape creates a tunnel of clear view but obscures the mucosa directly surrounding the distal end of the endoscope. Unlike conventional distal endoscopic attachments, the windows of the endoscopic assistance devices enable viewing of intestinal mucosa at the periphery of the distal end of the endoscope. Furthermore, treatment devices, such as, for example, scissors, tweezers, scalpels, or any cutting, cauterizing, or coagulating tools, can be extended out an operative channel of the endoscope and through the windows at any angle. The resilience of the cage is an additional advantage over conventional distal attachments. The bars of the cage can bend to move around tight curves or wide polyps. The resilience of the bars causes them to push back on the tissue, allowing the cage to function as a tissue retractor to spread tissue aside and further facilitate the advance of the endoscope. The tissue retracting feature also enables movement of the tissue to positions that allow for easier access by a treatment device. Because the endoscopic assistance device does not occupy the operative channel, treatment devices can pass without having to compete for space with a conventional tissue retractor. While the devices and methods disclosed herein are described in the context of gastrointestinal endoscopy, they may also have utility in urology, arthroscopy, and laparoscopic surgery.

FIG. 1 shows a conventional endoscope 1. At its proximal end, a conventional endoscope 1 can include a light guide connector 2 and a light guide tube 3. The light guide connector can connect the endoscope 1 to a light source and/or a video system. The light guide connector 2 can also serve as the connection point for suction, gas, and/or liquid. The light guide tube 3 extends distally from the light guide connector 2 and connects at its distal end to the control body 4. The light guide tube 3 houses various channels and connecting cables for suction, gas, liquid, light (e.g., fiber optics), the video system(s), and electrical grounds. The control body 4 can include a camera mount, channel openings for operating instruments, and user controls 5, which can include angulation control knobs, controls for treatment tools, controls for gas or liquids, video switches, focusing controls, and controls for the physical handling of the (e.g., tension, steering, etc.) insertion tube 6. An elongated and flexible insertion tube 6 extends distally from the control body 4. The insertion tube 6 contains the channels and cables for the optical systems and the treatment systems, and protection for the internal components. During use, the insertion tube 6 is navigated through the anatomy to position its distal region 7 for optimal viewing and treatment of an area of interest. At its distal region 7, the insertion tube 6 includes a bending section 8 that can be articulated to navigate the anatomy and to best view an area of interest. The distal face 9 of the endoscope 1 includes exits for treatment or operative channels. For example, treatment tools can exit the distal face 9 via an operative channel, and liquid or gas can enter or exit the distal face 9 via nozzles or suction portals. The distal face 9 can also include objective lenses and light guides.

Figure 2:
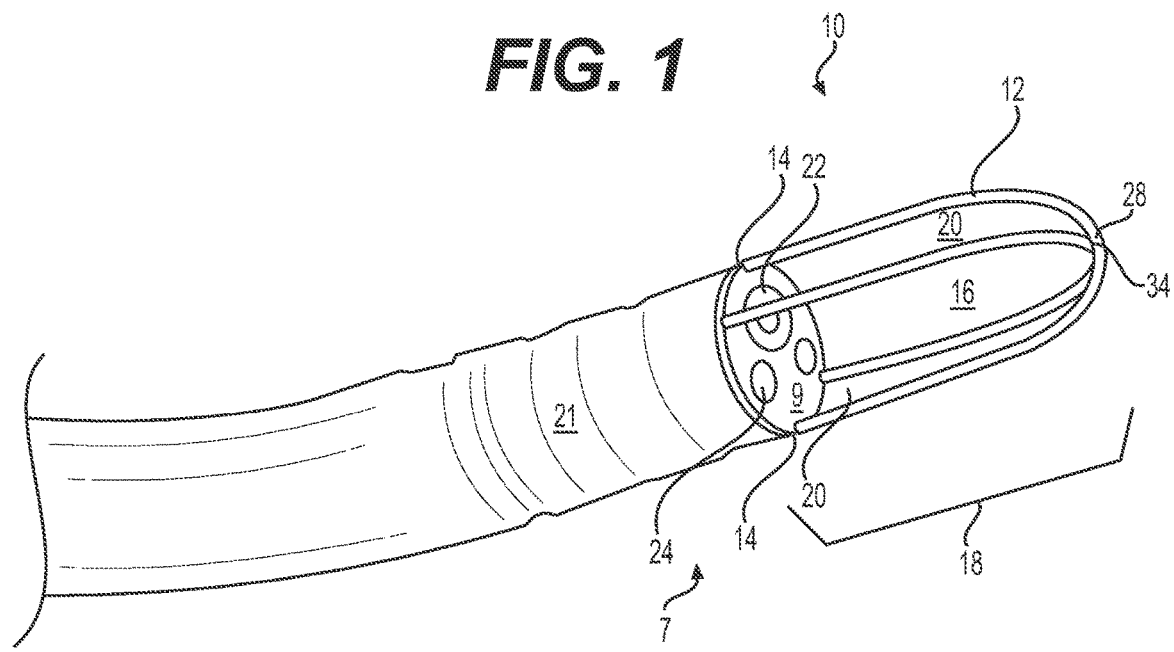
FIG. 2 shows an endoscope having an example embodiment of an endoscopic assistance device affixed to the distal face.
Figure 3:
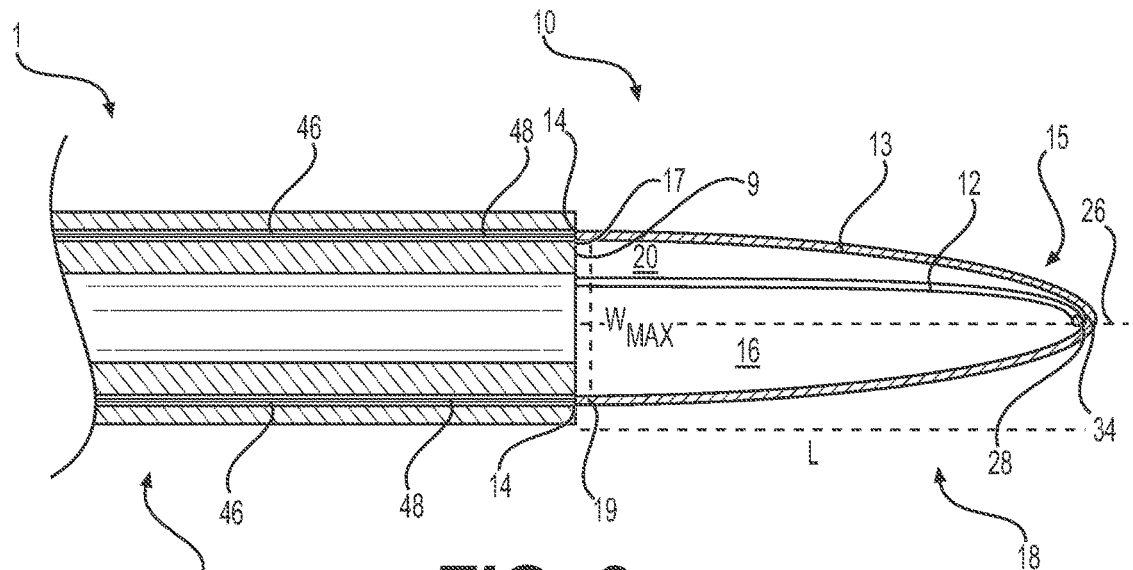
FIG. 3 shows a longitudinal cross sectional view the distal region of an endoscope and the endoscopic assistance device shown in FIG. 2.

FIG. 2 shows the distal region 7 of an endoscope having an example endoscopic assistance device 10 attached directly to distal face 9. One or more resilient, curved bars 12 extend from attachment points 14 around an internal void space 16 to form a resilient, curved cage 18 that spreads tissue gently during the advance of the endoscope. The resilient, curved bars 12 define the windows 20 of the cage 18 that enable the visualization of the surrounding tissue via an objective lens 22. Windows 20 also allow the passage of treatment devices from the operative channel 24 to access surrounding tissue. As shown in FIG. 3, the internal void space 16 extends radially outward from a central longitudinal axis 26 (extending out the distal face 9) to the windows 20 of cage 18. In the embodiment of FIG. 3, the windows 20 extend from the distal tip 28 of the cage down to the distal face 9 of the endoscope, such that a peripheral view of the surrounding tissue is unobstructed by the endoscopic assistance device 10.

Figure 4:
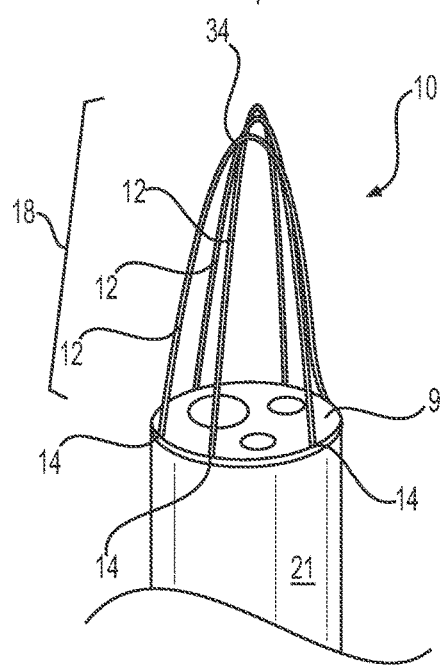
FIG. 4 shows an embodiment of an endoscopic assistance device.
Figure 5:
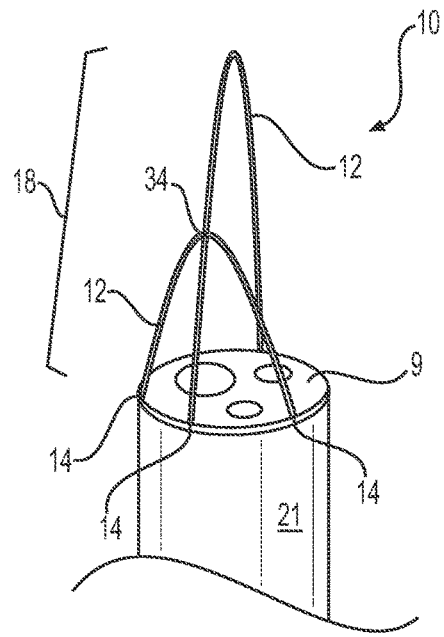
FIG. 5 shows another embodiment of an endoscopic assistance device.

In some embodiments, a bar 12 may extend, fully and uninterrupted, around the internal void 16 of the cage 18 to form an arch. In FIG. 3, selected bar 13 demonstrates the formation of arch 15, which extends fully around internal void 16 from a first end 17 to a second end 19. In the embodiment shown in FIG. 3, for example, the first and second ends 17, 19 of the arch 15 are attached directly to distal face 9 of the endoscope at attachment points 14. In other embodiments, the ends of bars and/or arches can be attached to the distal face 9 indirectly via a connecting device (described below). FIGS. 4 and 5 demonstrate alternative embodiments wherein the bars 12 form full arches that connect at their first and second ends directly to the distal face 9 of the endoscope. As used herein, the term bar may be used to indicate a bar that has an end connected to the endoscope, to a connecting device, or to another bar. The term arch is used to indicate a bar with both ends connected to the endoscope or to a connecting device. Regions along the length of an arch may be connected to other bars, for example, via fixation points, as described below. However, the ends of an arch are connected to the endoscope or to a connecting device.

A cage 18 may have any number of bars or arches defining any number of windows. For example, the embodiments shown in FIGS. 2 and 3 have two bars 12, each in the arch formation. Together, these two arches define four windows 20. The embodiment of FIG. 4 has three bars 12, each in the arch formation. Together, these three arches define six windows 20. In some embodiments, a single bar may be arched around the interior void 16 to form just two windows 20. The bars 12 of the embodiments shown in FIGS. 2-5 are directly, fixedly attached to the endoscope 1 at attachment points 14. The bars 12 could be, for example, bonded or welded to the distal face 9 or to the distal outer surface 21 of the endoscope. Or, in some embodiments, the proximal ends of the bars 12 could be slid and locked into specialized holes or slots on the distal face 9 or the distal outer surface 21. For example, the proximal ends of the bars 12 might be textured or have surfaces that interlock with surfaces of the specialized holes or slots, creating an interlocking mechanism. The interlocking mechanism can potentially be designed to release the bars 12 if desired by the practitioner (for example, to utilize the bars 12 as staples, as described below).

As shown in FIG. 3, the greatest width of the cage, $W_{max}$, can be measured at the widest position between two bars located opposite a longitudinal axis that extends through the cage. $W_{max}$ is measured perpendicular to a longitudinal axis 26 that extends out the distal face 9 of the endoscope 1 and through the cage 18. $W_{max}$ is measured when the bars are in a relaxed configuration (i.e., not under any tension or compression that might be induced during a procedure). Because the bars 12 of the cage 18 are attached, either directly to the endoscope 1 or indirectly to the endoscope (via a relatively narrow connecting device, as described below), $W_{max}$ is similarly sized to the diameter of the distal end of the endoscope. In other words, the cage 18 does not significantly widen the cross-sectional profile of the distal end of the endoscope 1. This is an advantage for procedures that take place in the non-insufflated, collapsed gastrointestinal lumen because the width of the cage does not distend the lumen to a greater extent than the endoscope itself distends the lumen. By keeping the cross-sectional diameter of the device to a minimum, the risk of injury and/or discomfort to the patient is minimized. In some embodiments, $W_{max}$ is at most three times the outer diameter of the endoscope. In some embodiments, such as the one shown in FIG. 3, $W_{max}$ occurs just adjacent the distal face 9 of the endoscope. However, this may not always be the case. In some embodiments, the resilience of the bars may cause the cage to widen slightly as it extends distally from the distal face 9 of the endoscope before narrowing again towards distal tip 28. In some embodiments, the bars may be shaped to position $W_{max}$ at any desired location along the length of the cage.

The length of the cage, L, is measured from the distal face 9 of the endoscope to the distal tip 28 of the cage. Length L can be any number from about 5 millimeters to about 40 millimeters, including about 5 millimeters, about 10 millimeters, about 15 millimeters, about 20 millimeters, about 25 millimeters, about 30 millimeters, about 35 millimeters, and about 40 millimeters.

Figure 6A:
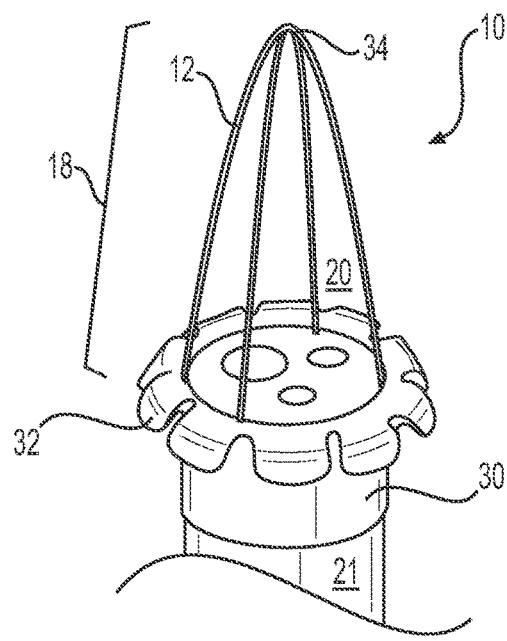
FIG. 6A shows an embodiment of an endoscopic assistance device including a connecting device.
Figure 6B:
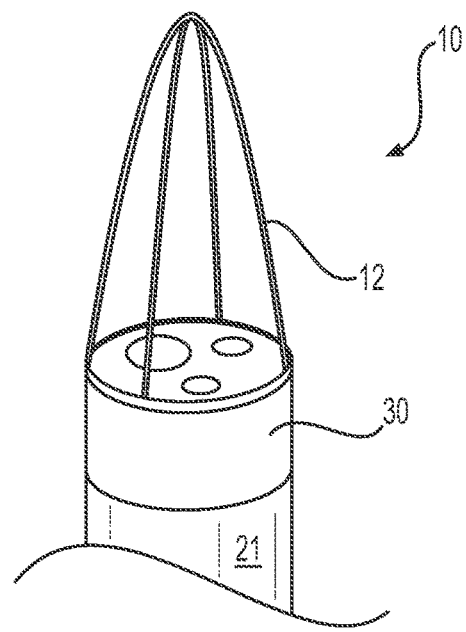
FIG. 6B shows another embodiment of an endoscopic assistance device including a connecting device.

FIGS. 6A and 6B show embodiments of endoscopic assistance devices 10 that include a connecting device 30. In these embodiments, first and second ends of each bar 12 are attached to a connecting device 30 that is a ring positioned around the distal outer surface 21 of the endoscope. The connecting device 30 can have additional features that further assist the advance of the endoscope within the bodily lumen, such as the flexible appendages 32 shown in FIG. 6A. For example, the attachable structures described in U.S. Patent Application Publication No. 2017/0049299, which is incorporated by reference in its entirety, describe a connecting device in the shape of a ring including flexible appendages 32. Alternatively, the connecting device 30 can be a ring that stretches around the distal outer surface 21 without including flexible appendages. The proximal ends of the bars 12 can be bonded, welded, or otherwise attached to the connecting device 30. In some embodiments, the proximal ends of the bars 12 can be slid and locked into specialized holes or slots on the connecting device 30. The proximal ends of the bars 12 can be textured or have surfaces that interlock with surfaces of the specialized holes or slots, creating an interlocking mechanism, for example.

The connecting device 30 does not extend significantly past the distal face 9 of the endoscope, ensuring that the peripheral view of the surrounding tissue is not obscured by the endoscopic assistance device 10. In some embodiments, every portion of the connecting device 30 is positioned proximal to the distal face 9 of the endoscope. In other embodiments, the distal portion of the connecting device 30 may protrude slightly past the distal face 9 of the endoscope, so long as the peripheral view is not significantly obstructed. The connecting device 30 also does not significantly widen the diameter of the distal end of the endoscope. In some embodiments, the thickness of the wall of the connecting device 30 (as measured perpendicularly to a longitudinal axis extending through the connecting device) can be from about 0.2 millimeters to about 2.5 millimeters, including about 0.2 millimeters, about 0.4 millimeters, about 0.6 millimeters, about 0.8 millimeters, about 1 millimeter, about 1.2 millimeters, about 1.4 millimeters, about 1.5 millimeters, about 1.6 millimeters, about 1.8 millimeters, about 2 millimeters, about 2.2 millimeters, about 2.4 millimeters, and about 2.5 millimeters. This is an advantage for procedures that take place in the non-insufflated, collapsed gastrointestinal lumen because the lumen is not extended to a significantly greater extent than if it were used alone. By keeping the cross-sectional diameter of the endoscopic assistance device 10 to a minimum, the risk of injury and/or discomfort to the patient is minimized. If, for example, a connecting device 30 embodiment having a wall thickness of about 2.5 millimeters is used, and the bars of the cage are connected on the exterior of the connecting device, then $W_{max}$ of the cage could be approximately the width of the endoscope plus about 5 millimeters (the wall thickness of both sides of the connecting device 30).

The connecting device 30 is relatively short by comparison to the length of the insertion tube 6 of the endoscope 1 so that it does not alter the flexibility properties of the insertion tube 6. For example, in some embodiments, the length of the connecting device 30 (as it extends along the length of the endoscope) can be up to about 10 millimeters. This short length ensures that the flexibility of central and proximal regions of the insertion tube 6 are unchanged by the use of the connecting device 30, because it does not extend over these regions. This is in contrast to overtubes that can be used to introduce tissue retractors over an endoscope. Unlike a connecting device 30, a conventional overtube is typically much wider than an endoscope. Furthermore, a conventional overtube will extend along the length of the insertion tube 6 by much more than 10 millimeters. Typically, a conventional overtube extends along the entire length of the insertion tube 6. Even in the distal region of the insertion tube 6, where connecting device 30 is placed, the connecting device 30 can be designed from a highly flexible material that will not significantly affect the flexibility of that distal region.

The bars 12 of the cage 18 can be formed of any resilient material, or any material that allows the bar to bend and return to the original position. For example, pseudoelastic or superelastic metal alloys, such as nitinol, can be used to form the bars 12. Alternatively, the bars 12 can be formed of flexible, resilient plastics, or any other resilient material that is biocompatible. In some embodiments, the bars can be formed of a thermoresistant material. Each or all of the bars can be formed of the same material, or they can be formed of different materials. Each or all of the bars may be the same, or they may differ, in terms of the degree of resilience, rigidity, strength, and/or thickness. The bars 12 can vary extensively in thickness, but will not be so thick as to significantly obstruct the view from the distal face 9 of the endoscope through the windows 20, to block the movement of treatment devices through said windows, or to overly hinder the flexibility of the cage 18. The thickness of a bar 12 is measured as the distance extending from the outer surface of the bar 12, perpendicularly past a longitudinal axis extending through the bar 12, and to the oppositely positioned outer surface of the bar 12. In some embodiments, two or more bars 12 can be twisted into a set of twisted bars (described in more detail below with respect to FIGS. 12 and 13), to alter the resilience properties of the cage 18. In some embodiments, a thick bar can be joined at a fixation point 38 with a thinner bar to custom tailor the movement and resilience of the cage 18.

The bars 12 will come into direct contact with the intestinal mucosa, and as such, will have rounded outer surfaces to minimize trauma and to ensure that they do not cut the mucosa. For example, the bars can be circular or oval in a cross section taken transverse to the longitudinal axis of the bar. The rounded surfaces facilitate sliding along the intestinal mucosa. In some embodiments, additional lubrication of the outer surfaces of the bars can be achieved, for example, by applying a lubricating coating or utilizing a material with a low coefficient of friction to form the bars or to form an outer layer of the bars.

The bars 12 are able to move in ways that allow them to bend and swivel in response to the changing anatomy, easing access of the endoscope 1 through a wide variety of anatomical structures (such as, for example, very wide polyps or sharp turns) while limiting the impact of the endoscopic attachment device 10 on the intestinal mucosa. The bars can, for example, swivel, or rotate, with respect to a plane formed by the bent bar or arch. In some embodiments, the bars 12 can swivel anywhere from about 0 to about 180 degrees with respect to the plane formed by the bent bar or arch, including about 1 degree, about 10 degrees, about 20 degrees, about 30 degrees, about 40 degrees, about 50 degrees, about 60 degrees, about 70 degrees, about 80 degrees, about 90 degrees, about 100 degrees, about 110 degrees, about 120 degrees, about 130 degrees, about 140 degrees, about 150 degrees, about 160 degrees, about 170 degrees, and about 180 degrees. The bars can also move back and forth in a direction approximately perpendicular to the plane formed by the bent bar or arch. The back and forth movement can occur simultaneously with the rotation, or separately from the rotation.

In the endoscopic assistance devices 10 shown in FIGS. 2-6, the bars 12 cross each other. The crossing point 34 of two bars 12 can be centered with respect to a longitudinal axis 26 extending out the distal face 9 endoscope (i.e. at the apogee or distal tip 28 of the cage 18, as shown in FIG. 2). Alternatively, the crossing point 34 can be positioned off center with respect to the longitudinal axis, as shown in FIG. 5, for example, to create a larger window 20 for viewing the intestinal mucosa. The crossing point 34 could be positioned, for example, relatively close to the distal face 9 of the endoscope 1. The length of the bar 12 (as measured from the first end to the second end) can be varied to accomplish an off-centered crossing point.

Figure 7:
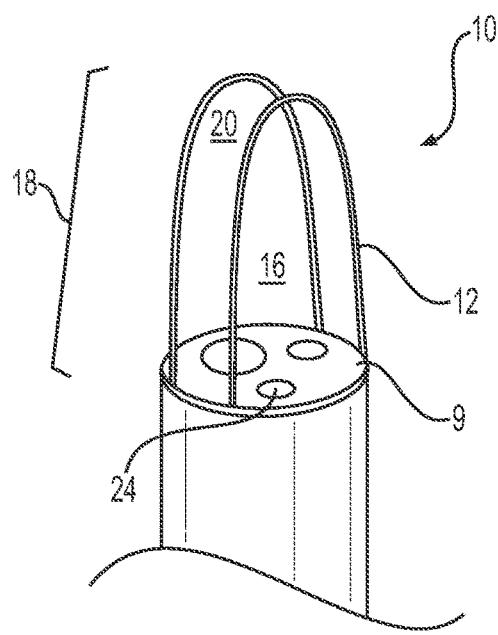
FIG. 7 shows another embodiment of an endoscopic assistance device.

Some embodiments of endoscopic assistance devices 10 have bars 12 that do not cross or contact each other. Such an embodiment is shown in FIG. 7. The cage 18 is formed of two resilient curved bars 12, each arched around the internal void 16 of the cage 18. The bars 12 form a total of three windows 20 to enable visualization of tissue lying distal to the distal face 9. The windows 20 also enable the exit of treatment devices extending out the operative channel 24 to access the tissue.

The extent to which the cage 18 morphs and bends in response to pressure from the anatomy depends in part on how the bars 12 interact with each other. As described above with respect to FIG. 7, each of the bars 12 can extend from the endoscope (or, alternatively, from a connecting device 30) without coming into contact with any other bar 12. As such, the arch formed by the bar 12 is independently movable and rotatable. The movement of an independent arch is not typically affected by the movement other bars or arches of the cage. The independent arch may contact another part of the endoscopic assistance device 10 when under strain, for example, when bent by contact with the intestinal wall. However, due to the resilient properties, the independent arch will then return to its relaxed position, unconstrained by other bars or arches of the cage. By contrast, the bars 12 shown in FIGS. 2-6 cross each other.

Depending on the length of each bar 12, the bars may or may not come into contact with each other at the crossing point 34. If they do, their movement may be restricted by the contact with the other bar 12. If they do not contact at the crossing point 34, they may remain independently movable unless strained to the point at which they do contact each other.

Figure 8:
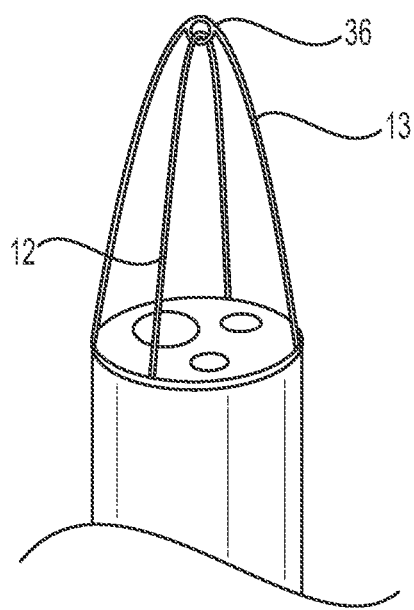
FIG. 8 shows another embodiment of an endoscopic assistance device.

In some embodiments, such as the one shown in FIG. 8, a first, inner bar 12 may extend through a loop 36 on an outer bar 13. Or, two or more bars may rotate around each other to form a set of twisted bars (described in more detail below with respect to FIGS. 12 and 13), and a third bar may extend through a gap formed by the twisting bars. In these embodiments, the movement of a bar 12 is partially dependent on the movement of the other bar or bars. For example, the inner bar 12 shown in FIG. 8 can move independently until it contacts the side of the loop 36 of the outer bar 13 (or the side of the gap formed by the twisting bars in FIGS. 12 and 13), at which point the two bars will move simultaneously.

Figure 9:
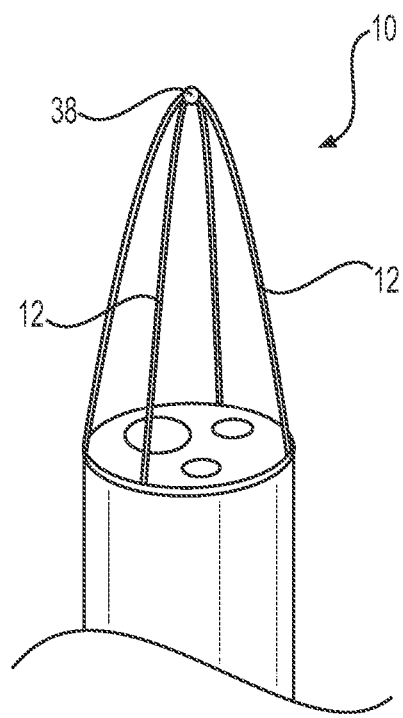
FIG. 9 shows another embodiment of an endoscopic assistance device.
Figure 10:
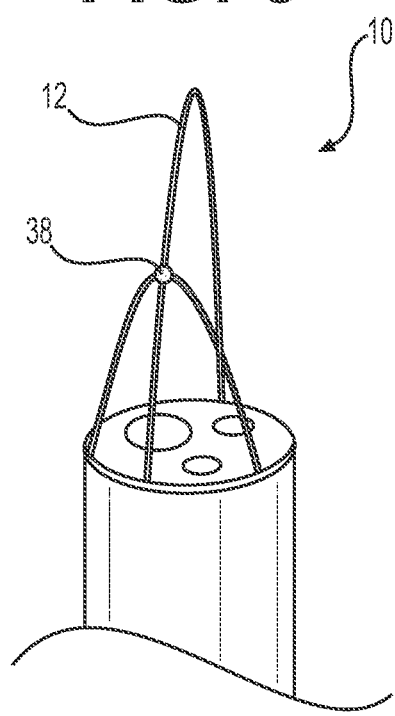
FIG. 10 shows another embodiment of an endoscopic assistance device.
Figure 11:
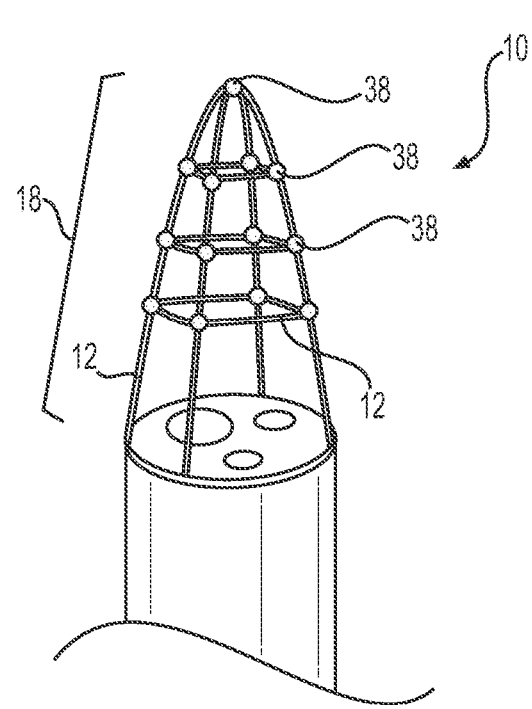
FIG. 11 shows another embodiment of an endoscopic assistance device.

FIG. 9 shows an embodiment in which the bars 12 are fastened to each other at a fixation point 38. Fixation of the bars 12 causes the movement of one to cause movement of the other. The fixation point 38 can be centered along the longitudinal axis of the scope, as shown in FIG. 9, or the fixation point can be off center as shown in FIG. 10. Fixation of two bars can be accomplished, for example, via bonding, welding, or molding. In some embodiments, such as the one shown in FIG. 11, the first and second ends of a given bar 12 can be attached at fixation points 38 to other bars of the cage, and not necessarily to the endoscope 1 or to a connecting device 30 (see, for example, the bars 12 extending parallel to the distal face 9 of the endoscope). The bars 12 can extend in any direction in relation to the longitudinal axis 26 of the endoscope, and any number of bars can be used to create a cage 18 with any number of windows. For example, a cage 18 can be constructed of 1, 2, 3, 4, 5, 6, 7, 8, 9, 10, 11, 12, 13, 14, 15, 16, 17, 18, 19, 20 or more bars 12 connected either directly to the endoscope 1, to a connecting device 30 that connects to the endoscope, or to another bar 12.

Figure 12:
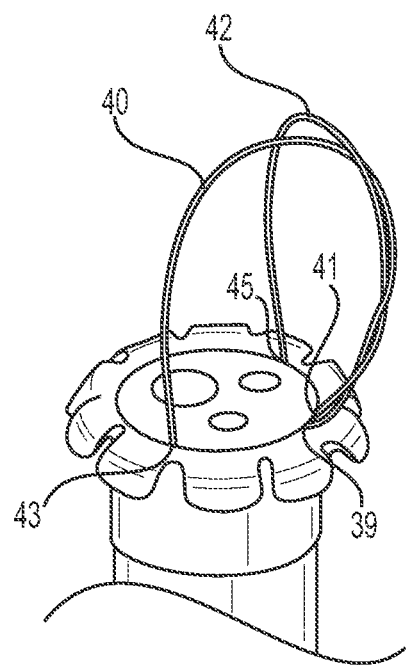
FIG. 12 shows another embodiment of an endoscopic assistance device.
Figure 13:
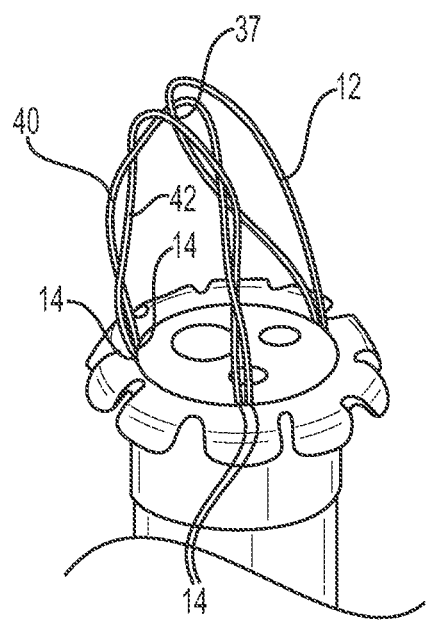
FIG. 13 shows another embodiment of an endoscopic assistance device.

FIGS. 12 and 13 show embodiments wherein the cage 18 comprises two or more twisted bars that rotate around each other. FIG. 12 shows an embodiment with two twisted bars 40, 42. FIG. 13 shows an embodiment with two twisted bars 40, 42 and a third bar 12 that extends through a gap 37 formed between the two twisted bars 40, 42. The two or more twisted bars 40, 42 may twist around each other along their entire length, such that they are positioned adjacent each other at all attachment points 14 (at both their first and second ends, as shown in FIG. 13). Alternatively, the two or more twisted bars 40, 42 may twist around each other along only a portion of their length (partially twisted bars), as shown in FIG. 12. When two or more bars are twisted along only a portion of their length, their attachment points 14 at a selected set of bar ends may be directly adjacent each other, or the attachment points 14 at a selected set of bar ends may be spread around the circumference of the endoscope or connecting device. For example, in the embodiment shown in FIG. 12, the first end 39 of the first twisted bar 40 and the first end 41 of the second twisted bar 42 have attachment points 14 that are directly adjacent to each other, while the second end 43 of the first twisted bar 40 and the second end 45 of the second twisted bar 42 are circumferentially spread from each other at the attachment points 14. The two or more twisted bars can be twisted around each other anywhere from one rotation (360 degrees) to ten rotations (3600 degrees), including 1 rotation, 1.5 rotations, 2 rotations, 2.5 rotations, 3 rotations, 3.5 rotations, 4 rotations, 4.5 rotations, 5 rotations, 5.5 rotations, 6 rotations, 6.5 rotations, 7 rotations, 7.5 rotations, 8 rotations, 8.5 rotations, 9 rotations, 9.5 rotations, or 10 full rotations.

Some embodiments of the endoscopic assistance device 10 can include a retraction mechanism that enables adjustment of the length, L, of the cage 18 (defined as in FIG. 3), or adjustment of the length of one or more bars 12 of the cage. The length of an individual bar 12 can be defined along the portion which extends past the distal face of the endoscope. For example, the embodiment shown in FIG. 3 includes a retraction mechanism in the form of an elongated pull wire 46. The distal end 48 of the pull wire 46 is fastened to the end 17 of bar 12 and the proximal end of the pull wire 46 is configured to be manipulated by a user to affect the movement of the bar 12 in relation to the distal face 9 of the endoscope 1. The pull wire 46 can extend through the insertion tube 6 of the endoscope 1 or along the outer surface 21 of the endoscope 1. In some embodiments, the pull wire 46 can extend through a path that extends through a side of a connecting device 30 (such as the one shown in FIG. 6). For example, the path could run parallel to the longitudinal axis 26 of the endoscope 1. As an example of the utility of this feature, one bar 12 can be used during advancement of the endoscope to separate the tissue, then retracted to widen windows 20 for viewing a particular anatomical feature or to pass a large treatment device. Shortening of the cage 18 may also be useful, for example, when rounding a curve during advancement of the scope. In embodiments where the bars 12 widen slightly as they extend distally from the endoscope or the connecting device, shortening the cage can change the position of $W_{max}$, which widens the lumen closer to the lens of the endoscope.

Figure 14:
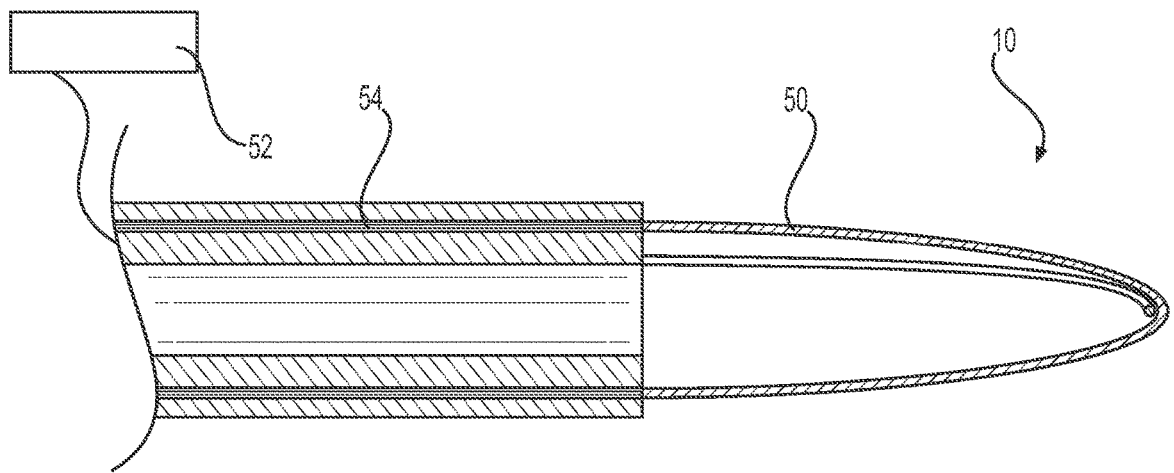
FIG. 14 shows an embodiment of an endoscopic assistance device including an electrically conductive bar.

Some embodiments of the endoscopic assistance device 10 can include at least one bar 50 that is electrically conductive. This can be useful for delivering an electric current as a treatment. For example, the electrically conductive bar 50 can be used to cauterize tissue. An exemplary diagram is shown in FIG. 14. The at least one electrically conductive bar 50 can be in electrical communication with a power source 52, either indirectly via radio or inductive transmission, or directly via electrical wiring 54. Electrical wiring 54 can extend through the insertion tube 6 of the endoscope 1 or along the outer surface 21 of the endoscope 1. In some embodiments, the electrical wire 54 might extend through a path that extends through a side of a connecting device 30 (such as the one shown in FIG. 6). For example, the path could run parallel to the longitudinal axis 26 of the endoscope 1.

The electrically conductive bar 50 can include an insulating coating over the majority of the bar, with one or more small gaps in the insulating coating for delivering current to an adjacent tissue. In some embodiments, a region of an electrically conductive bar 50 adjacent the distal face 9 of the endoscope 1 is electrically insulated, for example, by a plastic material, whereas the distal most region of electrically conductive bar 50 remains uninsulated and electrically conductive to create a bar with an electrically conductive tip. The insulated region of the bar could cover, for example, about 50% of the total surface area, about 60% of the total surface area, about 70% of the total surface area, about 75% of the total surface area, about 80% of the total surface area, about 85% of the total surface area, about 90% of the total surface area, or about 95% of the total surface area of the electrically conductive bar 50.

In some embodiments, one or more bars 12 can be detached from the cage 18 and/or endoscope 1 for therapeutic use. For example, a bar 12 may be released into the tissue for use as a staple. Such a bar may have one or two sharpened or barbed ends to facilitate its advance through the tissue. In such an embodiment, the endoscope may be equipped with a detachment feature that enables the release of the bar, and/or a guiding device that extends out from the operative channel and routes the released bar to the correct location in the tissue. The endoscope can be equipped with a suctioning device to hold the tissue during stapling. In some embodiments, one end of an arched bar may be released from the endoscope before the other end. The resilience of the bar causes it to straighten, and the distal face of the endoscope can be used to push the elongated bar into the tissue. The endoscope can include a closure device to facilitate the closure of the released bar/staple around the tissue.

Figure 15:
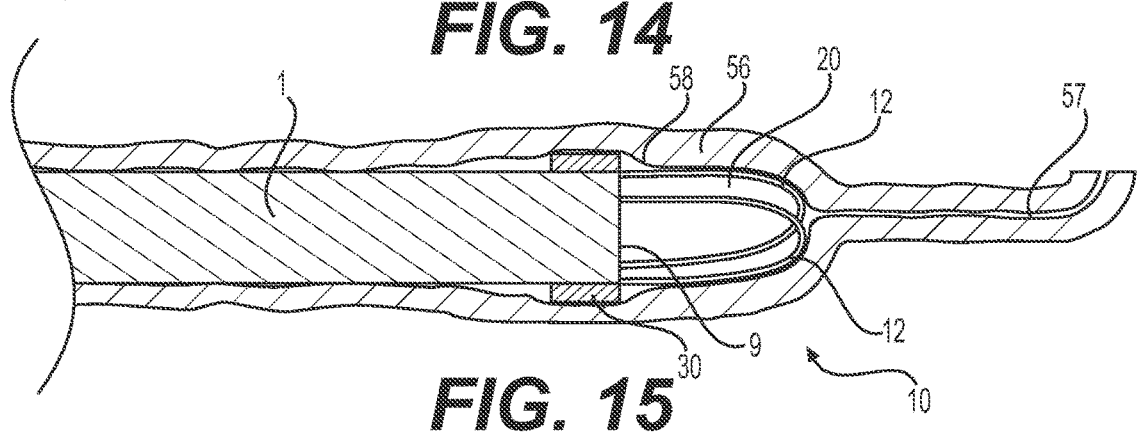
FIG. 15 shows an endoscopic assistance device being used to assist the advancement of an endoscope through a collapsed gastrointestinal lumen.
Figure 16:
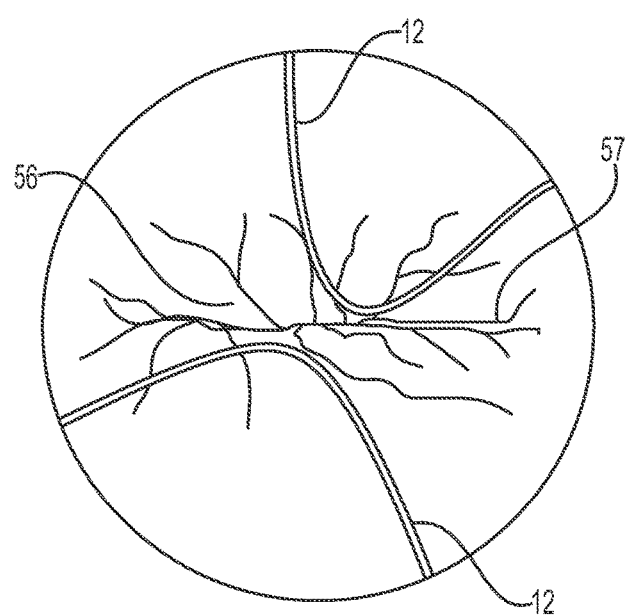
FIG. 16 shows the view of the gastrointestinal lumen and the endoscopic attachment device via the distal face of the endoscope.

Methods of using the endoscopic assistance devices 10 to assist the movement of an endoscope 1 through a collapsed, non-insufflated lumen are also disclosed herein. The methods can include providing an endoscope 1 having an endoscopic assistance device 10 affixed to the distal face 9. The resilient, curved bars 12 of cage 18 can be attached directly to the endoscope 1, or indirectly attached via a connecting device 30. The endoscope 1 and the endoscopic assistance device 10 are inserted into the collapsed gastrointestinal lumen. As shown in FIG. 15, the resilient, curved bars 12 of the device 10 move aside the walls 56 of the collapsed gastrointestinal lumen 57 adjacent the distal face 9 of the endoscope 1. The walls of the collapsed lumen are imaged via the windows 20 of the endoscopic assistance device 10. The peripheral view of the tissue 58 immediately adjacent the distal face 9 of the endoscope is not obscured by the device 10. The advance of the endoscope is facilitated, and any damaging impact of the distal face 9 on the tissue is decreased by the resilient, curved bars 12 of the device 10. The endoscope 1 can be rotated in order to adjust the position of one or more bars 12 to better facilitate the advance of the endoscope. For example, FIG. 16 shows the view out the distal face 9 of the endoscope. Bars 12 are visible in front of the lens 22. Rotation of the endoscope 1 can change the position of bars 12 until a less resistant area of tissue is found. At that point, the bars will more easily spread the tissue 56, opening collapsed lumen 57 to facilitate the advance of the endoscope 1.

Treatment devices can be advanced out the distal face 9 of endoscope and through windows 20 of the cage 18, for example, in order to cut, tweeze, or coagulate the walls 56 of the lumen 57. The bars 12 can be used to place the walls 56 of the lumen 57 under tension or compression, for example, to immobilize and facilitate access to the walls for subsequent treatment. In some cases, placing the tissue under tension using the bars can help with visualization of certain anatomical features that may need treatment, such as cutting or cauterizing. In some embodiments, the cage 18 itself is used as a treatment device, as described above. For example, the bars 12 of the cage can be used to deliver an electrical current to the walls 56 of the lumen 57. In some example methods, one or more of the bars 12 can be released into the walls 56 of the lumen, for example, in order to staple the walls 56 of the lumen. The walls of the lumen may be manipulated to ensure proper positioning of the releasable bar during stapling. Positioning the staple can include suctioning the walls of the lumen to facilitate positioning of the releasable bar/staple, use tweezers to hold the lumen, use of a guiding device to position the staple, or any combination of the above.

Some embodiments of the method can include adjusting the length of the cage 18 while the endoscope is inserted into the lumen 57. A retraction mechanism, such as, for example, the pull wire 46 (as shown in FIG. 3 and described above) can be used to retract the bar 12 into the distal region 7 of the endoscope 1, thereby altering the length L of the cage 18.

In another embodiment, one or more of the bars 12 of the cage 18 can be used as an endoclip. For example, a first bar may be formed of a shape memory metal alloy material. A second bar may be formed of a thin polymer material. The first bar can be positioned near an anatomical feature that requires an endoclip. A suction is applied to the walls of the anatomical feature to bring it into the interior void 16 of the cage. Once positioned, the second, thin polymer bar can be retracted into the distal face 9 of the endoscope 1, which triggers the release of the first bar to clip the captured anatomical feature.

In some embodiments, a transparent balloon may be positioned within the cage to facilitate viewing of the walls. Certain embodiments of balloons that might be utilized inside the cage are described in U.S. Pat. No. 9,833,126, which is incorporated by reference in its entirety. A transparent balloon can be helpful for ensuring a clear path of optical transmission by protecting the lens, especially when fluid or digestive matter obscure the view from the distal face of the endoscope. However, any cage described herein can be used without a balloon and still provide the advantages discussed herein.

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

What is claimed is:

1. An endoscopic assistance device comprising;
   a proximal connecting device comprising a stretchable ring, the stretchable ring defining a proximal end of the endoscopic assistance device, the stretchable ring further defining an inner diameter and being directly attachable to and removable from a distal end of an endoscope by stretching the stretchable ring around the endoscope, such that the inner diameter increases from an original diameter to a second, larger diameter,
   a resilient, curved cage defining a distal end of the endoscopic assistance device, the cage being attached to the proximal connecting device and extending distally therefrom and comprising one or more resilient, curved bars arranged to partially surround an internal void of the cage, a selected one of the one or more resilient, curved bars extending continuously around the internal void of the cage to form an arch formed solely of the selected curved bar, the arch having a first end attached to the proximal connecting device and a second end attached to the proximal connecting device,
   wherein a full length of the endoscopic assistance device measures 50 millimeters or less from the proximal end of the endoscopic assistance device to the distal end of the endoscopic assistance device, wherein the one or more resilient, curved bars at least partially define at least two windows of the cage, wherein the at least two windows are configured to enable visualization of tissue lying distal to the distal end of the endoscope, and wherein the at least two windows are configured to provide exit paths for treatment devices extending from the distal end of the endoscope and through the internal void.

2. The endoscopic assistance device of claim 1, wherein the proximal connecting device is not configured to alter the flexibility of a central or proximal region of an insertion tube of the endoscope.

3. The endoscopic assistance device of claim 1, wherein each of the one or more resilient, curved bars has a rounded external surface.

4. The endoscopic assistance device of claim 1, wherein the one or more resilient, curved bars comprises two or more resilient, curved bars that partially define at least three windows of the cage.

5. The endoscopic assistance device of claim 4, wherein the two or more resilient, curved bars do not contact or cross each other.

6. The endoscopic assistance device of claim 4, wherein the two or more resilient, curved bars of the cage are attached to each other at one or more fixation points.

7. The endoscopic assistance device of claim 4, wherein the two or more resilient, curved bars cross each other while remaining independently movable.

8. The endoscopic assistance device of claim 7, wherein the two or more resilient, curved bars comprise a first, inner bar extending through a loop on a second, outer bar.

9. The endoscopic assistance device of claim 1, wherein the one or more resilient, curved bars comprise two or more twisted bars that rotate around each other, wherein first and second ends of each of the two or more twisted bars are attached to the proximal connecting device.

10. The endoscopic assistance device of claim 9, wherein the one or more resilient, curved bars further comprises a third bar that extends between the two or more twisted bars.

11. The endoscopic assistance device of claim 1, wherein each of the one or more resilient, curved bars is bendable.

12. The endoscopic assistance device of claim 11, wherein each of the one or more resilient, curved bars extends continuously around the internal void of the cage to form an arch formed solely of the respective resilient, curved bar, each arch being a smoothly curving, bendable arch having a first end attached to the proximal connecting device and a second end attached to the proximal connecting device.

13. The endoscopic assistance device of claim 12, wherein the endoscopic assistance device is a gastrointestinal endoscopic assistance device.

14. The endoscopic assistance device of claim 1, wherein at least one of the one or more resilient, curved bars comprises textured ends for removably interlocking with an endoscope.

15. The endoscopic assistance device of claim 1, wherein at least one of the one or more resilient, curved bars is detachable from the cage via a release mechanism for use as a staple or an endoclip.

16. The endoscopic assistance device of claim 1, wherein a length of the cage is 40 millimeters or less.

17. The endoscopic assistance device of claim 1, wherein the arch extends within a plane, and the arch is freely rotatable about the plane.

18. The endoscopic assistance device of claim 17, wherein the arch is freely movable in a direction perpendicular to the plane.

19. An endoscopy system comprising;

an endoscope comprising a distal end and an endoscopic assistance device, the endoscopic assistance device comprising: a proximal connecting device comprising a stretchable ring, the stretchable ring defining a proximal end of the endoscopic assistance device, the stretchable ring further defining an inner diameter and being directly attachable to and removable from the distal end of the endoscope by stretching the stretchable ring around the endoscope, such that the inner diameter increases from an original diameter to a second, larger diameter, a resilient, curved cage attached to the proximal connecting device and extending distally therefrom, the cage comprising one or more resilient, curved bars arranged to partially surround an internal void of the cage, a selected one of the one or more resilient, curved bars extending continuously around the internal void of the cage to form an arch formed solely of the selected curved bar, the arch having a first end attached to the proximal connecting device and a second end attached to the proximal connecting device, wherein the one or more resilient, curved bars at least partially define at least two windows of the cage, wherein the at least two windows are configured to enable visualization of tissue lying distal to the distal end of the endoscope, and wherein the at least two windows are configured to provide exit paths for treatment devices extending from the distal end of the endoscope and through the internal void.

20. The endoscopy system of claim 19, wherein the cage has a greatest width $W_{max}$ measured perpendicularly to a longitudinal axis extending through the cage when the cage is in a relaxed position, and wherein $W_{max}$ is not more than three times an outer diameter of the endoscope.

* * * * *